US007853406B2

(12) United States Patent
Michelson et al.

(10) Patent No.: US 7,853,406 B2
(45) Date of Patent: Dec. 14, 2010

(54) PREDICTIVE TOXICOLOGY FOR BIOLOGICAL SYSTEMS

(75) Inventors: Seth Gary Michelson, San Jose, CA (US); Alex Lawrence Bangs, San Carlos, CA (US)

(73) Assignee: Entelos, Inc., Foster City, CA (US)

( * ) Notice: Subject to any disclaimer, the term of this patent is extended or adjusted under 35 U.S.C. 154(b) by 906 days.

(21) Appl. No.: 10/462,108

(22) Filed: Jun. 13, 2003

(65) Prior Publication Data
US 2004/0254736 A1 Dec. 16, 2004

(51) Int. Cl.
*G01N 33/48* (2006.01)
(52) U.S. Cl. ...................................................... 702/19
(58) Field of Classification Search .................... 702/19
See application file for complete search history.

(56) References Cited

U.S. PATENT DOCUMENTS

| | | | |
|---|---|---|---|
| 5,657,255 A | 8/1997 | Fink et al. | |
| 5,808,918 A | 9/1998 | Fink et al. | |
| 5,947,899 A | 9/1999 | Winslow et al. | |
| 6,108,635 A | 8/2000 | Herren et al. | |
| 6,132,969 A * | 10/2000 | Stoughton et al. | 435/6 |
| 6,421,612 B1 | 7/2002 | Agrafiotis et al. | |
| 6,542,858 B1 | 4/2003 | Grass et al. | |
| 2002/0091666 A1 | 7/2002 | Rice et al. | |
| 2002/0192671 A1 | 12/2002 | Castle et al. | |
| 2003/0009099 A1 | 1/2003 | Lett et al. | |
| 2003/0018457 A1 | 1/2003 | Lett et al. | |
| 2003/0027127 A1 | 2/2003 | Farr et al. | |
| 2003/0033127 A1 | 2/2003 | Lett | |

FOREIGN PATENT DOCUMENTS

| | | |
|---|---|---|
| WO | 00/65523 | 11/2000 |
| WO | 01/57775 | 8/2001 |
| WO | 01/98935 | 12/2001 |
| WO | 02/44992 | 6/2002 |

OTHER PUBLICATIONS

Frazier. Predictive Toxicodynamics: Empirical /Mechanistic Approaches. Toxicology in Vitro. 1997, vol. 11, pp. 465-472.*
Blanch et al. Biochemical Engineering. New York: Marcel Dekker, Inc. 1996, pp. 266-268.*
Rizzi et al. Xylose fermentation by yeasts. 5. Use of ATP balances for modeling oxygen-limited growth and fermentation of yeast *Pichia stipitis* with xylose as carbon source. Biotechnology and Bioengineering, vol. 34, 1989, pp. 509-514.*
Veech et al. The Time-course of the effects of ethanol on the redox and phosphorylation states of rat liver. Biochemical Journal. vol. 127, 1972, pp. 387-397.*
Waring et al. "Identifying Toxic Mechanisms using DNA Microarrays: Evidence that an Experimental Inhibitor of Cell Adhesion Molecules Expression Signals Through the Aryl Hydrocarbon Nuclear Receptor,"Toxicology (Dec. 2002) vol. 181-182, pp. 537-550.*
Waring et al. "Microarray Analysis of Hepatotoxins in vitro Reveals a Correlations Between Gene Expression Profiles and Mechanisms of Toxicity," Toxicology Letters (2001) vol. 120, pp. 359-368.*
Somogyi and Greller, "The dynamics of molecular networks: applications to therapeutic discovery," *Drug Discov. Today* 6, 1267-1277 (2001).
Hall et al, "Biosimulation: Dynamic Modeling of Biological Systems," *Annual Reports in Medicinal Chemistry*, 37; 279-288 (2002).
Dimasi, "New Drug Development in the United States from 1963 to 1999", *Clin. Pharmacol. Ther.* 69, 286-296 (2001).
Dimasi, "Risks in new drug development: Approval success rates for investigational drugs", *Clin. Pharmacol. Ther.* 69, 297-307 (2001).
Fielden et al., "In silico Approaches to Mechanistic and Predictive Toxicology: An Introduction to Bioinformatics for Toxicologists," *Crit Rev Toxicol*, 32, 67-112 (2002).
Vedani et al., "Internet Laboratory for Predicting Harmful Effects Triggered by Drugs and Chemicals. Concept and Call for Co-operation," *ALTEX*, 18, 110-114 (2001).
Werner, "Target gene identification from expression array data by promoter analysis," *Biomol Engr*, 17, 87-94 (2001).
Dominici et al., "Bayesian Semiparametric Analysis of Developmental Toxicology Data," *Biometrics* , 57, 150-157 (2001).
Brazma et al., "Gene expression data analysis," *FEBS Lett*, 480, 17-24 (2000).
Kim et al., "Predicting Carcinogenicity by Using Batteries of Dependent Short-Term Tests," *Environ Health Perspect*, 102 Suppl, 127-130 (1994).
Greene et al, "Knowledge-based expert systems for toxicity and metabolism prediction: DEREK, STAR, and METEOR, SAR QSAR," *Environ Res*, 10, 299-314 (1999).
Ridings et al., "Computer prediction of possible toxic action from chemical structure: an update on the DEREK system," *Toxicology*, 106, 267-279 (1996).
Barratt et al., "Validation and Subsequent Development of Derek Sensitization Rulebase by Analysis of the BgVV List of Contact Allergens," *J Chem Inf Comput Sci*, 39, 294-298 (1999).
Benfenati et al., "Computational predictive programs (expert systems) in toxicology," *Toxicology*, 119, 213-225 (1997).
Sandersdon et al., "Computer Prediction of Possible Toxic Action from Chemical Structure; The DEREK System," *Hum Exp Toxicology*, 10, 261-273 (1991).

(Continued)

*Primary Examiner*—Jerry Lin
(74) *Attorney, Agent, or Firm*—Karen E. Flick

(57) ABSTRACT

Methods and apparatus to identify a potential toxicity of a therapy in a biological system are described. In one embodiment, a method uses a computer model that represents a set of biological processes of the biological system. The method includes executing the computer model to identify a first set of biological processes contributing to the occurrence of a toxic state of the biological system. The method also includes identifying a set of biological assays based on the first set of biological processes and testing the therapy in the set of biological assays to identify a second set of biological processes modified by the therapy. The method further includes identifying the potential toxicity of the therapy based on the second set of biological processes.

12 Claims, 8 Drawing Sheets

OTHER PUBLICATIONS

Praisler et al. "Computer-Aided Screening for Hallucinogenic and Stimulant Amphetamines with Gas Chromatography-Fourier Transform Infrared Spectroscopy," *J Anal Toxicology*, 25, 45-56 (2001).

Soffers et al, "Computer-modeling-based QSARs for analyzing experimental data on biotransformation and toxicity," *Toxicol in Vitro*, 15, 539-551 (2001).

Trohalaki et al., "Improved QSARs for predictive toxicology of halogenated hydrocarbons," *Comput Chem*, 24, 421-427 (2000).

Rucki et al., "Acute toxicity of alcohols: prediction by QSAR analysis and by molecular similarity," *Cent Eur J Public Health*, 5, 183-187 (1997).

Grant et al., "Modeling the mouse lymphoma forward mutational assay: the Gene-Tox program database," *Mutation Res*, 465, 201-229 (2000).

El-Masri, H. A. et al., "Physiologically Based Pharmacokinetic/Pharmacodynamic Modeling of Chemical Mixtures and Possible Applications in Risk Assessment", Toxicology 1995, vol. 105, pp. 275-282.

Hall, A.H., "Computer Modeling and Computational Toxicology in New Chemical and Pharmaceutical Product Development", Toxicology Letters Dec. 1998, vol. 102-103, pp. 623-626.

Derendorf, et al., "Modeling of pharmacokinetic/pharmacodynamic (PK/PD) relationships: concepts and perspectives." Pharmaceutical Research, vol. 16, No. 2, pp. 176-185, Feb. 1999.

* cited by examiner

PREDICTIVE TOXICOLOGY FOR BIOLOGICAL SYSTEMS

COPYRIGHT NOTICE

A portion of the disclosure of the patent document contains material that is subject to copyright protection. The copyright owner has no objection to the facsimile reproduction by anyone of the patent document, as it appears in the Patent and Trademark Office patent file or records, but otherwise reserves all copyright rights whatsoever.

FIELD OF THE INVENTION

The field of the invention relates to predictive toxicology. For example, methods and apparatus for identifying a potential toxicity of a therapy in a biological system are described.

BACKGROUND OF THE INVENTION

Drug development can be roughly divided into four stages: discovery, pre-clinical testing, clinical testing, and regulatory approval. As part of the drug discovery process, a biological process or biological constituent can be identified as a valid target for therapeutic modulation (i.e., target identification and validation). Next, the drug discovery process typically shifts to the development of a compound that can interact with that target in a therapeutically appropriate manner (i.e., lead identification and development). But to take a compound and turn it into a drug, the compound should be optimized and made drug-like. That begs the question: "What is optimal or what criteria should be used to select a particular compound for subsequent stages of drug development?" When dealing with the interaction of a compound with a complex network of biological processes, achieving an "optimum" is, mathematically speaking, a multivariate problem. In other words, the compound should be acceptable on multiple fronts, including being efficacious, displaying appropriate accessibility measures (e.g., absorption, distribution, metabolism, and excretion measures), and displaying appropriate pharmacokinetic and pharmacodynamic measures. Moreover, the compound should be safe at doses anticipated for therapeutic efficacy.

The costs required to successfully bring new drugs to market are enormous and continue to rise. The large numbers of drugs that fail during pre-clinical and clinical testing are a significant contribution to these costs. In particular, about 53 percent of drugs fail during Phase II of clinical trials. A significant proportion of these failures arises due to unexpected system-wide effects associated with a complex network of biological processes that underlie human physiology. For example, biological redundancies and regulatory feedback control mechanisms can react to molecular interventions from drugs in unexpected ways and can contribute to the incidence of adverse or toxic events.

Currently, criteria for advancing compounds into subsequent stages of drug development are often incomplete and poorly predict the compounds' clinical effects. To reduce drug development costs and improve clinical success rates, it would be desirable to eliminate early those compounds that are predicted to produce toxic events.

Previous attempts in predictive toxicology include bioinformatics techniques and chemoinformatics techniques. Bioinformatics techniques typically attempt to predict biological response to a compound based on analysis and statistical modeling of gene and protein expression data, while chemoinformatics techniques typically attempt to predict biological response to a compound by associating chemical characteristics of the compound with a particular biological response.

While bioinformatics techniques can correlate changes in gene or protein expression data with a particular physiological condition, such techniques are generally incapable of independently and directly identifying causal relationships. In other words, changes caused by a physiological condition often cannot be distinguished from changes that cause the physiological condition. Moreover, bioinformatics techniques often cannot predict how changes in gene or protein expression data, which are usually observed in isolated cells or tissue samples, may affect or be affected by a biological system as a whole.

Chemoinformatics techniques often require extensive knowledge of chemical shape, which knowledge can be captured in a vector space representation. In particular, chemoinformatics techniques sometimes attempt to segment a chemical shape space based on inferred associations between chemical shape and biological response. A drawback of such techniques is that knowledge of chemical shape is often incomplete and inconsistent, especially in a biologically relevant environment, such that chemical shape often cannot be accurately and completely characterized for vector space manipulation. As a result of the incomplete knowledge of chemical shape, the dimensionality of the problem is generally reduced by projecting the true vector space into a lower dimensional representation. However, when projecting into a lower dimensional representation, true distances in chemical shape space can become distorted, thus limiting the predictive value of chemoinformatics techniques.

It is against this background that a need exists to develop the methods and apparatus described herein.

SUMMARY OF THE INVENTION

In one innovative aspect, the invention relates to a method to identify a potential toxicity of a therapy in a biological system. In one embodiment, the method uses a computer model that represents a set of biological processes of the biological system. The method includes executing the computer model to identify a first set of biological processes contributing to the occurrence of a toxic state of the biological system. The method also includes identifying a set of biological assays based on the first set of biological processes and testing the therapy in the set of biological assays to identify a second set of biological processes modified by the therapy. The method further includes identifying the potential toxicity of the therapy based on the second set of biological processes.

In another innovative aspect, the invention relates to a computer-readable medium. In one embodiment, the computer-readable medium includes code to define a computer model that represents a set of biological processes of a biological system. The computer-readable medium also includes code to define a virtual stimulus. The virtual stimulus represents a modification to at least one biological process of the set of biological processes, and the modification is associated with a toxic state of the biological system. The computer-readable medium further includes code to execute the computer model based on the virtual stimulus to generate a virtual profile associated with the set of biological processes.

BRIEF DESCRIPTION OF THE DRAWINGS

For a better understanding of the nature and objects of some embodiments of the invention, reference should be made to the following detailed description taken in conjunction with the accompanying drawings, in which.

DETAILED DESCRIPTION OF SPECIFIC EMBODIMENTS

Figure 1:
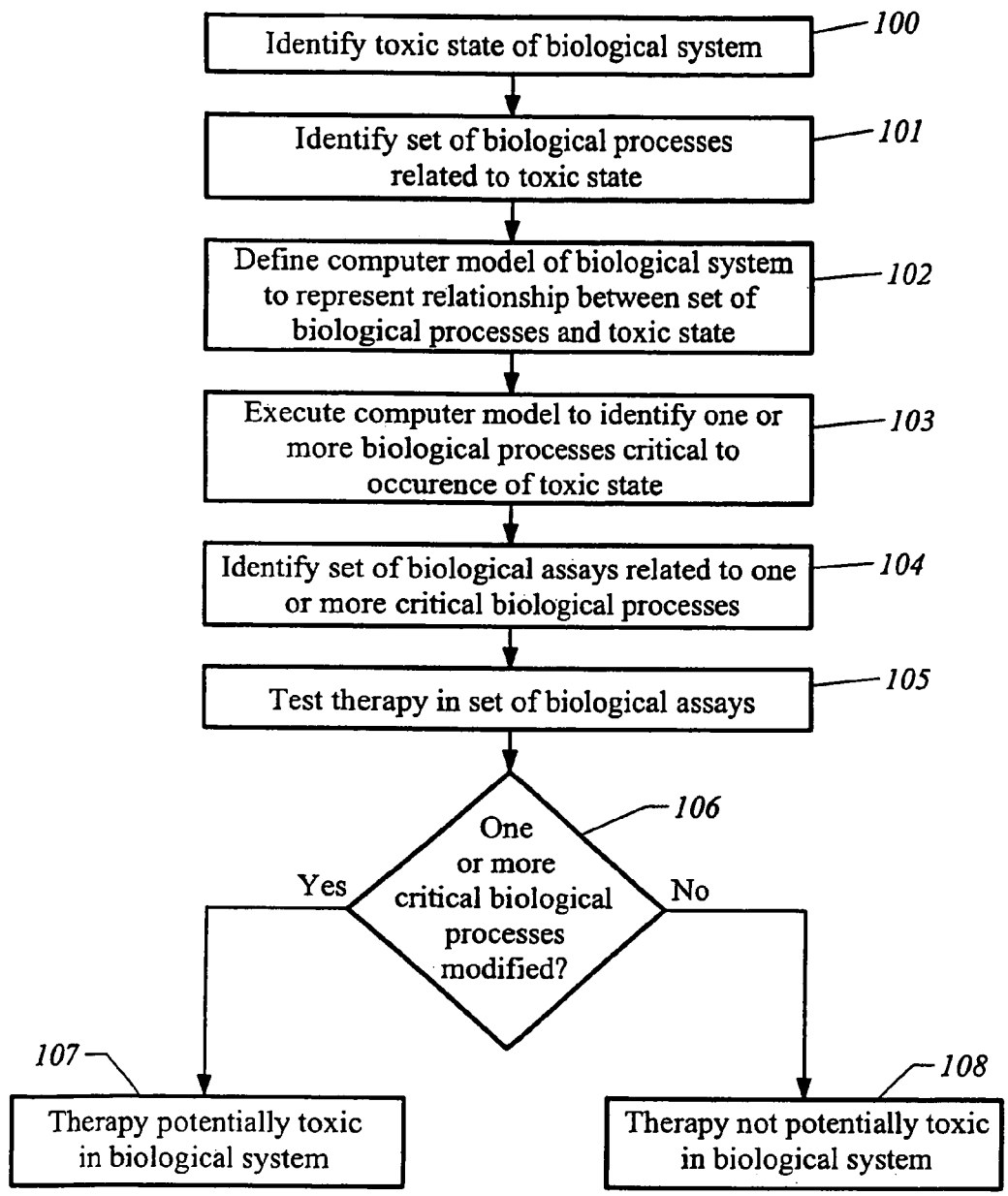
FIG. 1 shows a flow chart for identifying a potential toxicity of a therapy in a biological system, according to an embodiment of the invention.

Embodiments of the invention relate to predictive toxicology. For example, methods and apparatus for identifying a potential toxicity of a therapy in a biological system are described. In addition, methods and apparatus described herein can also be used to identify a susceptibility of a particular patient or a particular type of patient to toxicity of a therapy.

Some embodiments of the invention use computer models to identify a set of biological assays to adequately and accurately characterize biological response, such as, for example, biological response induced by an exogenous drug. By using computer models, underlying molecular and cellular dynamics that lead to toxic events can be identified. Execution of the computer models can provide criteria to identify biological assays that can characterize biological responses to therapies. In particular, the biological assays can serve to identify potential toxicities induced by therapies. In some instances, results of the biological assays can be used to identify patterns of biological response that can be to used categorize therapies into recognizable classes within a biological response space. Advantageously, therapies can be characterized based on observed biological response rather than based on biological response that is inferred from chemical characteristics.

Biological Systems, Biological States, Biological Constituents, and Biological Processes A "biological system" can include, for example, an individual cell, a collection of cells such as a cell culture, an organ, a tissue, a multi-cellular organism such as an individual human patient, a subset of cells of a multi-cellular organism, or a population of multi-cellular organisms such as a group of human patients or the general human population as a whole. A biological system can also include, for example, a multi-tissue system such as the nervous system, immune system, or cardio-vascular system.

A "biological state" refers to a condition associated with a biological system. In some instances, a biological state refers to a condition associated with the occurrence of a set of biological processes of a biological system. As used herein, the term "set" refers to a collection of one or more elements. Elements of a set can also be referred to as members of the set. Elements of a set can be the same or different. In some instances, elements of a set can share one or more common characteristics. Each biological process of a biological system can interact according to some biological mechanism with one or more additional biological processes of the biological system. As the biological processes change relative to each other, a biological state typically also changes. A biological state typically depends on various biological mechanisms by which biological processes interact with one another. A biological state can include, for example, a condition of a nutrient or hormone concentration in plasma, interstitial fluid, intracellular fluid, or cerebrospinal fluid. For example, biological states associated with hypoglycemia and hypoinsulinemia can be characterized by conditions of low blood sugar and low blood insulin, respectively. These conditions can be imposed experimentally or may be conditions present in a particular biological system. A biological state of a neuron can include, for example, a condition in which the neuron is at rest, a condition in which the neuron is firing an action potential, a condition in which the neuron is releasing a neurotransmitter, or a combination thereof. As another example, biological states of a collection of plasma nutrients can include a condition in which a person awakens from an overnight fast, a condition just after a meal, and a condition between meals.

A biological state can include a "toxic state," which refers to an abnormal or harmful condition associated with a biological system. A toxic state can be associated with an abnormal or harmful effect of a therapy or other stimulus in a biological system. In some instances, a toxic state refers to a condition associated with the occurrence of a set of biological processes of a biological system, where one or more of the biological processes play a role in an abnormal or harmful effect of a therapy or other stimulus in the biological system. A toxic state can be observed in, for example, a cell, an organ, a tissue, a multi-cellular organism, or a population of multi-cellular organisms. Examples of toxic states include conditions associated with cirrhosis, immunosuppression, nephrotoxicity, myelosuppression, tachycardia, irregular heartbeat, hypertension, and mutagenicity.

A "biological constituent" refers to a portion of a biological system. A biological constituent that makes up a biological system can include, for example, an extra-cellular constituent, a cellular constituent, an intra-cellular constituent, or a combination thereof. Examples of biological constituents include DNA; RNA; proteins; enzymes; hormones; cells; organs; tissues; portions of cells, tissues, or organs; subcellular organelles such as mitochondria, nuclei, Golgi complexes, lysosomes, endoplasmic reticula, and ribosomes; chemically reactive molecules such as $H^+$; superoxides; ATP; citric acid; protein albumin; and combinations thereof. Each biological constituent of a biological system can interact according to some biological mechanism with one or more additional biological constituents of the biological system. A biological mechanism by which biological constituents interact with one another may be known or unknown. A biological mechanism may involve, for example, a biological system's synthetic, regulatory, homeostatic, or control networks. The interaction of one biological constituent with another can include, for example, a synthetic transformation of one biological constituent into the other, a direct physical interaction of various biological constituents, an indirect interaction of various biological constituents mediated through intermediate biological events, or some other mechanism.

A "biological process" refers to an interaction or a set of interactions between biological constituents of a biological system. In some instances, a biological process refers to a set of biological constituents drawn from some aspect of a biological system together with a network of interactions between the biological constituents. Biological processes can include, for example, biochemical or molecular processes. Biological processes can also include, for example, processes that occur within or in contact with an environment of a cell, organ, tissue, or multi-cellular organism. Examples of biological processes include biochemical pathways in which molecules are broken down to provide cellular energy, biochemical pathways in which molecules are built up to provide cellular structure or energy stores, biochemical pathways in which proteins or nucleic acids are synthesized or activated, and biochemical pathways in which protein or nucleic acid precursors are synthesized. Biological constituents of such biochemical pathways include, for example, enzymes, synthetic intermediates, substrate precursors, and intermediate species.

Biological processes can also include, for example, signaling and control pathways. Biological constituents of such pathways include, for example, primary or intermediate signaling molecules as well as proteins participating in signaling or control cascades that usually characterize these pathways. For signaling pathways, binding of a signaling molecule to a receptor can directly influence the amount of intermediate signaling molecules and can indirectly influence the degree of phosphorylation (or other modification) of pathway proteins. Binding of signaling molecules can influence activities of cellular proteins by, for example, affecting the transcriptional state of a cell. These cellular proteins are often important effectors of cellular processes initiated by a signal. Control pathways, such as those controlling the timing and occurrence of cell cycles, share some similarities with signaling pathways. Here, multiple and often ongoing cellular events are temporally coordinated, often with feedback control, to achieve a consistent outcome, such as, for example, cell division with chromosome segregation. This temporal coordination is a consequence of the functioning of control pathways, which are often mediated by mutual influences of proteins on each other's degree of modification or activation (e.g., phosphorylation). Other control pathways can include pathways that seek to maintain optimal levels of cellular metabolites in the face of a changing environment.

Biological processes can be hierarchical, non-hierarchical, or a combination of hierarchical and non-hierarchical. A hierarchical process is one in which biological constituents can be arranged into a hierarchy of levels, such that biological constituents belonging to a particular level can interact with biological constituents belonging to other levels. A hierarchical process generally originates from biological constituents belonging to the lowest levels. A non-hierarchical process is one in which a biological constituent in the process can interact with another biological constituent that is further upstream or downstream. A non-hierarchical process often has one or more feedback loops. A feedback loop in a biological process refers to a subset of biological constituents of the biological process, where each biological constituent of the feedback loop can interact with other biological constituents of the feedback loop.

Therapies

A "therapy" refers to a type of stimulus or perturbation that can be applied to a biological system. In some instances, a therapy can affect a biological state of a biological system by known or unknown biological mechanisms. Therapies that can be applied to a biological system can include, for example, drugs, environmental changes, or combinations thereof.

Drugs refer to compounds of any degree of complexity that can affect a biological state, whether by known or unknown biological mechanisms, and whether or not used therapeutically. Examples of drugs include typical small molecules of research or therapeutic interest; naturally-occurring factors such as endocrine, paracrine, or autocrine factors or factors interacting with cell receptors of any type; intracellular factors such as elements of intracellular signaling pathways; factors isolated from other natural sources; pesticides; herbicides; and insecticides. Drugs can also include, for example, agents used in gene therapy like DNA and RNA. Also, antibodies, viruses, bacteria, and bioactive agents produced by bacteria and viruses (e.g., toxins) can be considered as drugs. A biological response to a drug may be a consequence of, for example, drug-mediated changes in the rate of transcription or degradation of one or more species of RNA, drug-mediated changes in the rate or extent of translational or post-translational processing of one or more polypeptides, drug-mediated changes in the rate or extent of degradation of one or more proteins, drug-mediated inhibition or stimulation of action or activity of one or more proteins, and so forth. In some instances, drugs can exert their effects by interacting with a protein. Drugs that increase rates or stimulate the level or activity of one or more biological constituents can be referred to as "activating drugs" or "agonists," while drugs that decrease rates or inhibit the level or activity of one or more biological constituents can be referred to as "inhibiting drugs" or "antagonists." For certain applications, drugs can also include, for example, compositions including more than one drug or compositions including one or more drugs and one or more excipients.

In addition to drugs, the methods described herein are also applicable to environmental changes that can affect a biological state, whether by known or unknown biological mechanisms, and whether or not used therapeutically. Examples of environmental changes include changes in temperature (e.g., a temperature elevation of 10° C.) and exposure to radiation. Other environmental changes can include, for example, changes relating to feeding behavior or nutritional intake (e.g., short-term fasting, long-term fasting, single meal per day, multiple meals per day, caloric preload prior to a meal, self-feeding until equilibrium weight is established, and diets with varying nutrient compositions), changes relating to levels of physical activity or exercise, or a combination thereof.

Moreover, the methods described herein are applicable to combinations of drugs, combinations of environmental changes, as well as combinations of one or more drugs and one or more environmental changes. For example, the methods described herein are applicable to combinations of drugs used to treat different conditions, such as, high blood pressure, arthritis, high blood cholesterol, and cancer. In some instances, various elements of such combinations can be applied to a biological system at the same level or at different levels. Also, various elements of such combinations can be applied to a biological system at the same time or at different times. For example, two drugs may be applied at the same dose or at different doses, and at the same time or at different times.

Mathematical Models of Biological Systems

The methods according to some embodiments of the invention can be implemented using a mathematical model that represents a set of biological processes of a biological system. In particular, the mathematical model can represent the set of biological processes using a set of mathematical relations. For instance, the mathematical model can represent a first biological process using a first mathematical relation and a second biological process using a second mathematical relation. A mathematical relation typically includes one or more variables that describe a behavior (e.g., time evolution) that can be simulated by the mathematical model. More particularly, mathematical relations of the mathematical model can define interactions among variables, where the variables can represent levels or activities of biological constituents of the biological system as well as levels or activities of combinations or aggregate representations of various biological constituents of the biological system. In addition, variables can represent various stimuli that can be applied to the biological system.

The behavior of variables can be influenced by a set of parameters included in a mathematical model. For example, parameters can represent initial values of variables, half-lives of variables, rate constants, conversion ratios, exponents, and curve-fitting parameters. The set of parameters can be included in mathematical relations of the mathematical model. In some instances, parameters can be used to represent intrinsic characteristics (e.g., genetic factors) as well as external influences (e.g., environmental factors) for a biological system.

Mathematical relations employed in a mathematical model can include, for example, partial differential equations; ordinary differential equations, both linear and nonlinear; stochastic differential equations; differential algebraic equations; difference equations; cellular automata; coupled maps; equations of networks of Boolean or fuzzy logical networks; or a combination thereof. In some instances, the mathematical relations of the mathematical model are ordinary differential equations that can take the form:

$$dx/dt = f(x,p,t),$$

where x is an N dimensional set of variables, t is time, dx/dt is the rate of change of x, p is an M dimensional set of parameters, and f is a function that represents interactions among the variables. For example, the mathematical relations can take the form:

$$V_C \frac{dC}{dt} = P - C \frac{V_C}{\tau_C}$$

$$V_I \frac{dI}{dt} = \frac{P}{F} - MCR \times I$$

where C(t), which represents c-peptide concentration, and I(t), which represents insulin concentration, form x, and the parameters $V_C$, $V_I$, P, MCR, F, and $\tau_C$ form p.

A representation of a biological state can include values or other indicia associated with variables, parameters, and/or biological processes at a specified time and for a specified execution scenario. In some instances, a biological state can be mathematically represented by values of x and p at a given time. The behavior of variables x can be simulated by, for example, numerical or analytical integration of one or more mathematical relations. For example, numerical integration of the ordinary differential equations defined above can be performed to obtain values for the variables x at various times and hence the evolution of the biological state over time.

Computer Models of Biological Systems

The methods according to some embodiments of the invention can be implemented using a computer model that defines a mathematical model of a biological system. Computer models according to some embodiments of the invention can be defined as, for example, described in the following references: Paterson et al., U.S. Pat. No. 6,078,739; Paterson et al., U.S. Pat. No. 6,069,629; Paterson et al., U.S. Pat. No. 6,051,029; Thalhammer-Reyero, U.S. Pat. No. 5,930,154; McAdams et al., U.S. Pat. No. 5,914,891; Fink et al., U.S. Pat. No. 5,808,918; Fink et al., U.S. Pat. No. 5,657,255; Paterson et al., PCT Publication No. WO 99/27443; Paterson et al., PCT Publication No. WO 00/63793; and Winslow et al., PCT Publication No. WO 00/65523; the disclosures of which are incorporated herein by reference in their entirety. Suitably, some embodiments of the invention can be implemented using the following commercially available computer models of biological systems: Entelos® Asthma PhysioLab® systems, Entelos® Metabolism PhysioLab® systems, and Entelos® Adipocyte CytoLab™ systems. Other computer models of biological systems can be used to implement some embodiments of the invention.

In some instances, a computer model used to implement some embodiments of the invention allows critical integrated evaluation of conflicting data and alternative hypotheses. The computer model can represent biological processes at a lower hierarchical level and evaluate the impact of these biological processes on biological processes at a higher hierarchical level. Thus, the computer model can provide a multi-variable view of a biological system. The computer model can also provide cross-disciplinary observations through synthesis of information from two or more disciplines into a single computer model or through linking two computer models that represent different disciplines.

A computer model used to implement some embodiments of the invention can be hierarchical and can reflect a particular biological system and anatomical factors relevant to issues to be explored by the computer model. The level of detail at which a hierarchy starts and the level of detail at which the hierarchy ends are often dictated by a particular intended use of the computer model. Because biological constituents being evaluated often operate at a subcellular level, the lowest level of the hierarchy can be the subcellular level. The subcellular level can include, for example, biological constituents such as DNA, mRNA, proteins, chemically reactive molecules, and subcellular organelles. Because an individual biological system is a common entity of interest with respect to the ultimate effect of the biological constituents, the individual biological system (e.g., represented in the form of clinical observables) can be at the highest level of the hierarchy.

A computer model can represent a normal state of a biological system. A virtual stimulus can be defined to simulate a stimulus or perturbation that can be applied to the biological system. For example, the computer model can contain parameters that when altered simulate the induction of a lesion that may lead to a toxic state of the biological system. By selecting and altering one or more parameters, a user can modify the normal state and induce a toxic state of interest. In some embodiments of the invention, selecting or altering one or more parameters can be performed automatically.

A computer model can be executed with or without virtual stimuli, thereby obtaining outputs for a biological system represented by the computer model. These outputs can correspond to a set of measurements of levels or activities of biological constituents represented by the computer model or measurements of any other behavior associated with a toxic state of interest.

For certain applications, a computer model can be configured to allow visual representation of mathematical relations as well as interrelationships between variables, parameters, and/or biological processes. This visual representation can include multiple modules or functional areas that, when grouped together, represent a large complex model of a biological system.

Figure 3:
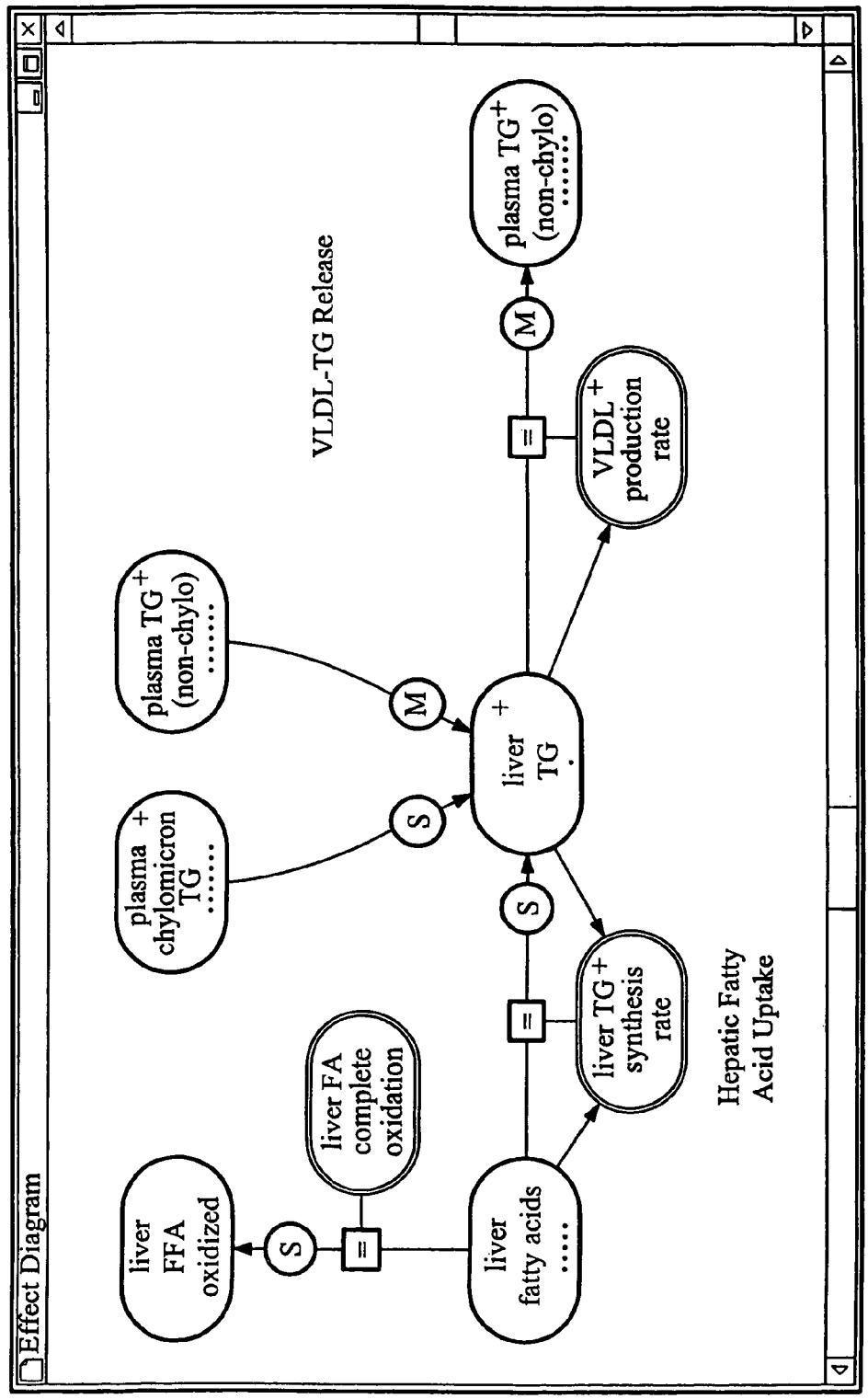
FIG. 3 shows an example of a module diagram of a computer model representing hepatic fatty acid uptake.

An example of a module diagram of a computer model representing hepatic fatty acid uptake, a potentially important pathway in the development of cirrhosis, is shown in FIG. 3. The nomenclature and symbols used in FIG. 3 describe the behavior and oxidation of free fatty acids in the liver and the conversion of these free fatty acids to hepatic triglycerides.

Referring to FIG. 3, the module diagram includes various nodes, which represent variables included in the computer model. In some instances, the nodes can also represent parameters and mathematical relations included in the computer model. Examples of nodes are discussed below.

State nodes, the single-border ovals shown in the module diagram, represent variables having values that can be determined by cumulative effects of inputs over time. Values of state nodes can be determined using differential equations. Parameters of a state node can include an initial value ($S_o$) and a status (e.g., value of the state node can be computed, held constant, or varied in accordance with specified criteria). A state node can have an additional parameter of half-life (h).

Function nodes, the double-border ovals shown in the module diagram, represent variables having values that, at a given point in time, can be determined by inputs at that same point in time. Values of function nodes can be determined using algebraic functions of their inputs. Parameters of a function node can include an initial value ($F_o$) and a status (e.g., value of the function node can be computed, held constant, or varied in accordance with specified criteria).

As shown in FIG. 3, arrows link various nodes to one another and represent relationships between the nodes. Examples of arrows are discussed below.

Conversion arrows, the thick arrows shown in the module diagram, represent the conversion of variables represented by connected nodes. A conversion arrow includes a circle that indicates a type of conversion. For example, the circle can be labeled as "M" to indicate a movement or "S" to indicate a change of state.

Argument arrows specify which nodes are inputs for function nodes.

Modifiers shown in the module diagram indicate the effects that nodes have on arrows to which they are connected. The types of effects are qualitatively indicated by symbols in the boxes shown in FIG. 3. For example, a node can allow Ⓐblock Ⓑregulate ⊟inhibit ⊡or stimulate ⊞a relationship represented by an arrow.

Figure 4:
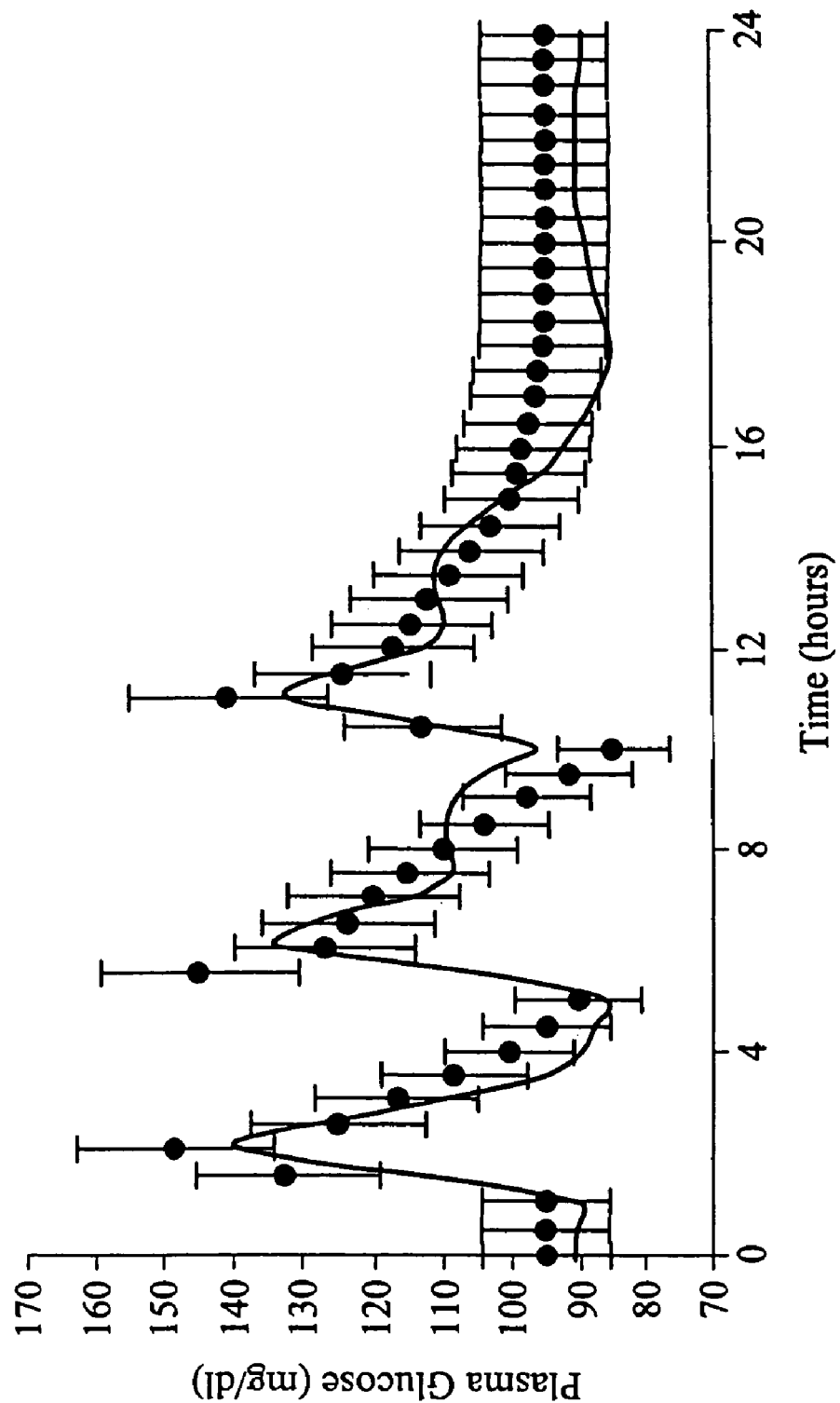
FIG. 4 shows an example of a comparison of plasma glucose levels predicted by a computer model (shown by the solid curve) and plasma glucose levels tracked in a free-feeding situation in volunteers who take part in a clinical study (shown by the sequence of data points).

Outputs of a computer model can be compared with actual clinical data, in vitro data, or in vivo data. FIG. 4 shows a comparison of plasma glucose levels predicted by a computer model (shown by the solid curve) and plasma glucose levels tracked in a free-feeding situation in volunteers who take part in a clinical study (shown by the sequence of data points).

For certain applications, a computer model can be used to define one or more configurations. Various configurations of a computer model can be associated with different representations of a biological system represented by the computer model. In particular, various configurations of the computer model can represent, for example, different variations of the biological system having different intrinsic characteristics, different external influences, or both. An observable condition (e.g., an outward manifestation) of a biological system can be referred to as its phenotype, while underlying conditions of the biological system that give rise to the phenotype can be based on genetic factors, environmental factors, or both. As one of ordinary skill in the art will understand, phenotypes of a biological system can be defined with varying degrees of specificity. In some instances, a phenotype can include an outward manifestation associated with a toxic state of interest. A particular phenotype typically can be reproduced by different underlying conditions (e.g., different combinations of genetic and environmental factors). For example, two patients may appear to be similarly overweight, but one could be overweight because of genetic susceptibility, and the other could be overweight because of diet and lifestyle choices. Various configurations of a computer model can be defined to represent different underlying conditions giving rise to a particular phenotype of a biological system. Alternatively, or in conjunction, various configurations of the computer model can be defined to represent different phenotypes of the biological system.

In some instances, a configuration of a computer model can be associated with a particular set of values for parameters of the computer model. Thus, a first configuration may be associated with a first set of parameter values, and a second configuration may be associated with a second set of parameter values that differs in some fashion from the first set of parameter values. One or more configurations of the computer model can be created based on an initial configuration that is associated with initial parameter values. A different configuration can be created based on the initial configuration by introducing a modification to the initial configuration, such as, for example, a modification to one or more of the initial parameter values. Alternative parameter values can be defined as, for example, disclosed in U.S. Pat. No. 6,078,739 discussed previously. These alternative parameter values can be grouped into different sets of parameter values that can be used to define different configurations of the computer model. Alternatively, or in conjunction, one or more configurations of the computer model can be created based on an initial configuration using linked simulation operations as, for example, disclosed in the co-pending and co-owned patent application to Paterson et al., entitled "Method and Apparatus for Conducting Linked Simulation Operations Utilizing A Computer-Based System Model", U.S. application Ser. No. 09/814,536, filed Mar. 21, 2001, the disclosure of which is incorporated herein by reference in its entirety.

Computer models used to implement some embodiments of the invention can be validated. Examples of techniques for validation are described in the co-pending and co-owned patent application to Paterson, entitled "Apparatus and Method for Validating a Computer Model", U.S. application Ser. No. 10/151,581, filed May 16, 2002, the disclosure of which is incorporated herein by reference in its entirety.

Computer System

Figure 2:
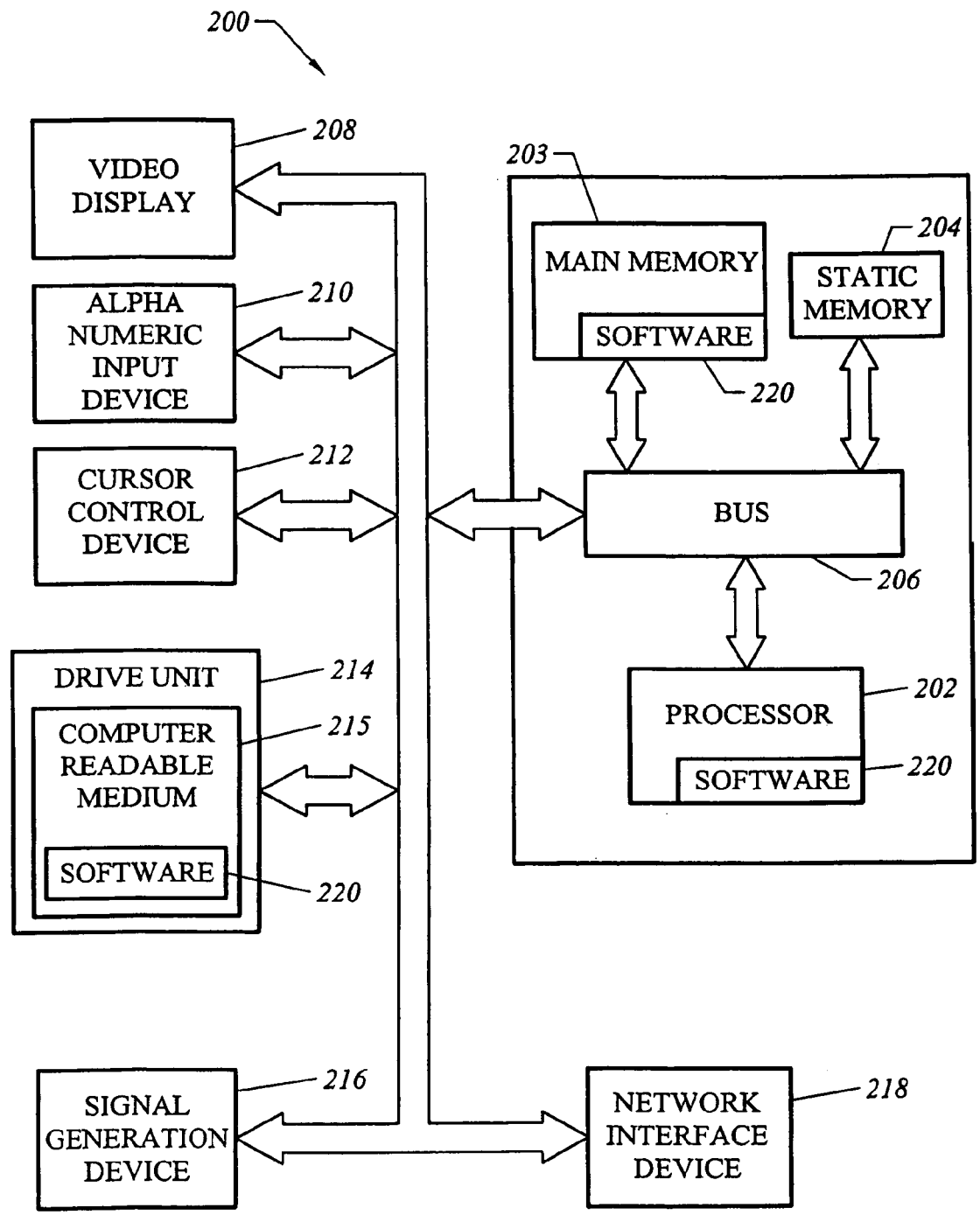
FIG. 2 shows a system block diagram of a computer system within which methods described herein can operate via software code, according to an embodiment of the invention.

FIG. 2 shows a system block diagram of a computer system 200 within which the methods described herein can operate via software code, according to an embodiment of the invention. The computer system 200 includes a processor 202, a main memory 203, and a static memory 204, which are coupled by bus 206. The computer system 200 can further include a video display unit 208 (e.g., a liquid crystal display ("LCD") unit or cathode ray tube ("CRT") display unit) on which a user interface can be displayed. The computer system 200 can also include an alphanumeric input device 210 (e.g., a keyboard), a cursor control device 212 (e.g., a mouse), a disk drive unit 214, a signal generation device 216 (e.g., a speaker), and a network interface device 218. The disk drive unit 214 includes a computer-readable medium 215 in which software 220 can be stored. The software 220 can also reside, completely or partially, within the main memory 203 and/or within the processor 202. The software 220 can also be transmitted or received via the network interface device 218. In some embodiments of the invention, one or more components of the computer system 200 are not included.

Methods to Identify a Potential Toxicity of a Therapy

The methods according to some embodiments of the invention can be used to identify a potential toxicity of a therapy in a biological system. In some instances, the methods can also be used to identify a susceptibility of a particular patient or a particular type of patient to toxicity of a therapy.

FIG. 1 shows a flow chart for identifying a potential toxicity of a therapy in a biological system, according to an embodiment of the invention. At step 100, a toxic state of the biological system is identified. The toxic state can be associated with, for example, cirrhosis, immunosuppression, nephrotoxicity, myelosuppression, tachycardia, irregular heartbeat, hypertension, or mutagenicity. At step 101, a set of biological processes related to the toxic state is identified. At step 102, a computer model of the biological system is defined. The computer model represents the set of biological processes and the interactions between the biological processes. In some instances, a previously developed computer model of the biological system can be used. At step 103, the computer model is executed to identify one or more biological processes critical to the occurrence of the toxic state. The one or more critical biological processes identified in step 103 can form, for example, a subset of the set of biological processes represented by the computer model. At step 104, a set of biological assays is identified. At least one biological assay from the set of biological assays is related to one or more of the biological processes identified as critical to the toxic state. At step 105, the therapy is tested in one or more of the identified biological assays. If one or more of the critical biological processes are modified (e.g., activated) (step 106), the therapy is identified as being potentially toxic in the biological system (step 107). If one or more of the critical biological processes are not modified (step 106), the therapy is identified as not being potentially toxic in the biological system (step 108).

The foregoing discussion provides a general overview of a method for identifying a potential toxicity of a therapy in a biological system, according to an embodiment of the invention. The following is a more detailed discussion of some of the operations shown in FIG. 1.

As used herein, the term "related to" and its grammatical equivalents refer to having a connection. For example, with reference to step 101, the set of biological processes related to the toxic state include, for example, biological processes that cause the toxic state, biological processes that affect the toxic state, biological processes that are modified by the toxic state, or a combination thereof. The set of biological processes can be identified based on information available to a user, information available in the art regarding the toxic state, or both. Information used to identify the set of biological processes can include, for example, experimental data, clinical data, knowledge or opinion of persons skilled in the art, outputs of a computer model, and other relevant sources.

For example, the toxic state of interest may be associated with the induction of cirrhosis by an exogenous drug. Cirrhosis is typically associated with liver fibrosis in which fibrotic scar tissue replaces normal tissue in a liver and causes dysfunction across the organ (e.g., bile duct blockage yielding jaundice or portal vein hypertension due to swelling around the portal vein). The identified set of biological processes can include, for example, biological processes that cause the liver fibrosis, biological processes that affect the liver fibrosis, biological processes that are modified as a result of the liver fibrosis, or a combination thereof. For example, biological processes related to cirrhosis can include biological processes associated with a whole body response to lysis of hepatocytes that are engorged with excess lipids (e.g., fatty acids). Such engorgement of the hepatocytes can be associated with a symptom known as "fatty liver." The lysis of the hepatocytes can also be associated with the release of liver enzymes into the blood stream, which leads to a symptom known as "elevated liver enzymes." The lysis of the hepatocytes can also induce a systemic inflammatory response that involves further cellular destruction and ultimate liver failure. Iteratively, biological processes controlling dynamics and changes in biological states can be identified. Also, biological constituents in the cascade of events can be identified.

Referring to step 102, the set of biological processes identified in step 101 are represented in the computer model of the biological system. For example, FIG. 3 shows a set of biological processes in a potentially important pathway in the development of cirrhosis. The computer model can be configured such that execution of the computer model allows for evaluation of the effect of one or more biological processes on the toxic state of interest.

Referring to step 103 of FIG. 1, the computer model is executed to identify one or more biological processes critical to the toxic state of interest. The computer model can be executed with or without a virtual stimulus. For example, in a normal homeostatic state, liver metabolism of lipids can be represented by a steady state solution to the computer model as shown in FIG. 3. In the case of cirrhosis, accumulation of lipids and the resultant toxicity can be represented in the computer model as a failure in a particular pathway or a failure associated with molecular dynamics surrounding that pathway. Introducing a modification to the computer model can represent an execution scenario associated with the toxic state. The modification can be introduced to represent, for example, an execution scenario in which a lipotoxic state takes over or in which there is a progression towards the lipotoxic state. For example, the modification can be introduced to represent overproduction of hepatic fatty acids (e.g., induced by an exogenous drug or excessive alcohol ingestion) that increases hepatic triglyceride concentrations. Such increase in hepatic triglyceride concentrations, in turn, can yield structural damage to the liver and can induce lysis and death of hepatocytes as well as elevated liver enzymes in the blood stream. The resulting cellular damage can produce liver fibrosis and scarring associated with cirrhosis or infection associated with hepatitis. In the case of cirrhosis, one or more of the events described above can act as a biomarker of cirrhosis. Execution of the computer model produces one or more outputs such as, for example, shown in FIG. 4. These outputs can be evaluated to identify one or more biological processes critical to the toxic state of interest.

In the case of cirrhosis, the toxic state can be represented as outputs associated with, for example, enzyme activities, product formation dynamics, and cellular functions that can indicate one or more biological processes that cause, affect, or are modified by the toxic state. Typically, the outputs of the computer model include a set of values that represent levels or activities of biological constituents or any other behavior of the toxic state. Based on these outputs, one or more biological processes can be designated as critical biological processes.

The computer model can be executed to represent a modification to one or more biological processes. In particular, a modification to a biological process can be represented in computer model to identify the degree of connection (e.g., the degree of correlation) between the biological process and the toxic state of interest. For example, a modification to a biological process can be represented in computer model to identify the degree to which the biological process causes, affects, or is modified by the toxic state. A biological process can be identified as causing the toxic state if a modification to this biological process is observed to produce the toxic state. In some instances, a modification to a biological process can be represented in the computer model to identify the degree of connection between other biological processes and the toxic state.

One or more mathematical relations representing a biological process can be modified to represent a modification to the biological process. A modification to a mathematical relation can include, for example, a parametric change (e.g., altering or specifying one or more parameter values associated with the mathematical relation), altering or specifying behavior of one or more variables associated with the mathematical relation, altering or specifying one or more functions associated with the mathematical relation, or a combination thereof. Alternative parameter values can be introduced as, for example, disclosed in U.S. Pat. No. 6,078,739 discussed previously. Also, linked simulation operations can be used to introduce modifications as, for example, disclosed in U.S. application Ser. No. 09/814,536 discussed previously.

In some instances, identifying critical biological processes can include sensitivity analysis. Sensitivity analysis can involve prioritization of biological processes that are related to the toxic state of interest. In some instances, sensitivity analysis can involve a rank ordering of biological processes based on their degree of connection to the toxic state. Sensitivity analysis allows a user to determine the importance of a biological process in the context of the toxic state. An example of a biological process of greater importance is a biological process that increases the severity of the toxic state. Thus, blocking or inhibiting the occurrence of this biological process can decrease the severity of the toxic state. In a rank ordering, a biological process that plays a more important role in the toxic state typically gets a higher rank. The rank ordering can also be done in a reverse manner, such that a biological process that plays a more important role gets a lower rank. Typically, biological processes that are identified as playing a more important role can be identified as critical biological processes.

Following identification of critical biological processes, the set of biological assays is identified at step 104. The set of biological assays can be designed to evaluate at least one of the critical biological processes.

Biological assays can include, for example, cell-based assays and animal models. Cell-based assays can be performed with, for example, acute cultures (e.g., cells surgically removed from human or animal tissue and then cultured in a dish) or cell line cultures (e.g., cells that have been transformed to immortalize them). Cells may be derived from normal humans or from humans having a toxic state or a disease. Cells may also be derived from non-human animals such as rats, mice, and so forth. For example, cells may be derived from normal non-human mammals or from non-human mammals that are animal models of obesity or diabetes. Animal models can include, for example, non-human mammals such as mice, rats, and so forth. The animal models used can include non-human mammals having a toxic state or a disease. For example, animal models of obesity or diabetes can include homozygous obese (ob), diabetic (db), fat (fat), or tubby (tub) mice.

For example, the set of biological assays can be designed to evaluate one or more pathways that induce cell lysis and death in the presence of increased hepatic triglycerides. The pathways that induce cell lysis and death can be identified using the computer model. In this example, a hepatocyte cell culture can be subjected to external stimuli that induce overproduction of fatty acids in intact liver cells. This overproduction, in turn, can result in the overproduction of hepatic triglycerides. Pathways that respond to the increased level of hepatic triglycerides, especially those that result in cell lysis and death, can yield biological responses (e.g., biological responses associated with enzyme activities, gene expression levels, and so forth) against which a predictive biological assay can be designed.

With reference to step 105 of FIG. 1, the therapy is tested in the set of biological assays. In some instances, different levels or amounts of the therapy can be tested in the set of biological assays to determine the level or amount at which the therapy is potentially toxic. For example, different doses of a drug can be tested in the set of biological assays to determine the dose at which the drug will be potentially toxic. As another example, different levels or amounts of various drugs or various environmental changes can be tested in the set of biological assays.

Following exposure to the therapy, the set of biological assays is evaluated to determine whether one or more of the critical biological processes are modified (step 106). Typically, modification of a critical biological process can be determined by evaluating the behavior of biological constituents that make up the critical biological process. In particular, levels or activities of the biological constituents can be determined. Another method of determining modification of a critical biological process involves evaluating changes in phenotype of a biological assay being studied.

To determine whether one or more of the critical biological processes are modified, transcription, translation, and/or activities of biological constituents can be measured. Measurement of transcription can be performed, for example, using a set of probes that include a set of polynucleotide sequences. For example, probes may include DNA sequences, RNA sequences, copolymer sequences of DNA and RNA, sequences of DNA analogs or mimics, sequences of RNA analogs or mimics, or combinations thereof. Polynucleotide sequences of probes may be synthesized nucleotide sequences, such as synthetic oligonucleotide sequences. These polynucleotide sequences can be synthesized enzymatically in vivo, enzymatically in vitro (e.g., by polymerase chain reaction), or non-enzymatically in vitro. The set of probes used can be immobilized to a solid support or surface, which may be porous or non-porous. For example, the set of probes may include polynucleotide sequences that are attached to a nitrocellulose or nylon membrane or filter. The set of probes can be implemented as hybridization probes as, for example, disclosed in Sambrook et al., Eds., Molecular Cloning: A Laboratory Manual, Vols. 1-3 (Cold Spring Harbor Laboratory, Cold Spring Harbor, N.Y., 2nd ed. 1989). A solid support or surface may be a glass or plastic surface. In some instances, measurement of transcription can be made by hybridization to microarrays of probes. A microarray typically includes a solid support or surface with an ordered array of binding or hybridization sites for products of various genes (e.g., a majority or substantially all of the genes) of a genome of a biological system. Such microarray can include a population of polynucleotide sequences (e.g., a population of DNA sequences or DNA mimics or a population of RNA sequences or RNA mimics) immobilized to the solid support or surface.

Measurement of translation can be performed according to several methods. For example, whole genome monitoring of proteins using "proteome" techniques can be performed by constructing a microarray in which binding sites include immobilized monoclonal antibodies specific to various proteins encoded by a genome. Antibodies can be present for a substantial fraction of the encoded proteins or at least for those proteins relevant to the action of the therapy being studied. Monoclonal antibodies can be produced as, for example, disclosed in Harlow and Lane, Antibodies: A Laboratory Manual (Cold Spring Harbor, N.Y., 1988). In some instances, monoclonal antibodies can be raised against synthetic peptide fragments, which are designed based on genomic sequence of a cell. For a monoclonal antibody array, proteins from a cell are contacted to the microarray, and binding of the proteins can be assayed with conventional techniques. Alternatively, proteins can be separated by two-dimensional gel electrophoresis systems as, for example, disclosed in Hames et al., Gel Electrophoresis of Proteins: A Practical Approach (IRL Press, New York, 1990); Shevchenko et al., 1996, Proc. Natl. Acad. Scie. U.S.A. 93:1440-1445; Sagliocco et al., 1996, Yeast 12:1519-1533; and Lander, 1996, Science 274:536-539. Two-dimensional gel electrophoresis typically involves iso-electric focusing along a first dimension followed by SDS-PAGE electrophoresis along a second dimension. The resulting electropherograms can be analyzed by numerous techniques, including, for example, mass spectrometric techniques, western blotting, immunoblot analysis using polyclonal and monoclonal antibodies, and internal and N-terminal micro-sequencing. Such techniques allow identification of a substantial fraction of proteins produced under given physiological conditions, including, for example, in cells (e.g., yeast) exposed to a drug or in cells modified by deletion or over-expression of a particular gene.

Measurement of activities of biological constituents, such as proteins, can be performed according to several methods. Measurement of activity can be performed by any functional, biochemical, or physical methods appropriate to the activity being characterized. Where the activity involves a chemical transformation, cellular protein can be contacted with a natural substrate, and the rate of transformation can be measured. Where the activity involves association in multimeric units (e.g., association of an activated DNA binding complex with DNA), the amount of associated protein or secondary consequences of the association (e.g., amounts of mRNA transcribed) can be measured. Also, where a functional activity is known, as in cell cycle control, performance of the functional activity can be measured.

With reference to FIG. 1, the potential toxicity of the therapy can be determined by evaluating the modification (if any) of one or more critical biological processes in the set of biological assays. A set of biological processes (e.g., critical biological processes) identified using the computer model can be compared with a set of biological processes modified by the therapy in the set of biological assays. The two sets of biological processes can be compared to produce a degree of correspondence of the two sets of biological processes.

As used herein, the term "degree of correspondence" and its grammatical equivalents refer to a relationship between two or more elements that are being compared. Examples of elements being compared include sets of biological processes and profiles of biological constituents. In some instances, the term "degree of correspondence" can describe the level of agreement, either mathematical or non-mathematical, between elements being compared. Mathematical agreement can include, for example, overlap in membership of two sets of elements (e.g., overlap in membership of two sets of biological processes) or statistical agreement (e.g., statistical agreement of two profiles of biological constituents). Non-mathematical agreement can include, for example, qualitative agreement between elements being compared.

The degree of correspondence between two sets of biological processes (e.g., one set identified using the computer model and the other set identified in the set of biological assays) can indicate the potential toxicity of the therapy of interest. If the two sets of biological processes correspond closely, then the therapy can be identified as having a high potential for inducing toxicity in the biological system. For example, a high potential for toxicity can be identified if most or all of the critical biological processes are modified in the set of biological assays. If the two sets of biological processes do not correspond closely, then the therapy can be identified as having a low potential for inducing toxicity in the biological system. For example, a low potential for toxicity can be identified if most or all of the critical biological processes are not modified in the set of biological assays.

For certain applications, a potential toxicity of a therapy can be identified by generating profiles of biological constituents. A virtual profile of biological constituents can be obtained from execution of a computer model, whereas an experimental or observed profile of biological constituents can be obtained from testing the therapy in a set of biological assays. A profile (e.g., a virtual or experimental profile) typically includes a set of values, and each value can be associated with one or more biological constituents. Typically, each value can be a numerical or non-numerical representation of the level or activity of one or more biological constituents. In some instances, the virtual profile of biological constituents can include a set of threshold or baseline values associated with a set of biological constituents.

For the virtual profile of biological constituents, the computer model can be executed to identify one or more biological processes related to a toxic state of interest. In some instances, the computer model can be executed to represent a modification to one or more biological processes. In particular, introducing a modification to the computer model can represent an execution scenario associated with the toxic state. For example, the modification can be introduced to represent overproduction of hepatic fatty acids that increases hepatic triglyceride concentrations. Execution of the computer model produces one or more outputs. As discussed above, outputs of the computer model typically include a set of values that represent levels or activities of biological constituents or any other behavior of the toxic state. These outputs can be evaluated to generate the virtual profile of biological constituents. In some instances, the virtual profile of biological constituents can serve as a biomarker of the toxic state. More particularly, the virtual profile can serve to predict or infer the occurrence of the toxic state and can be used as a diagnostic criteria or clinical sign of the toxic state.

For example, execution of the computer model can indicate that a particular pathway contributes to cell lysis and death in the presence of elevated hepatic triglycerides. A virtual profile can be generated to represent enzymatic activity or level of expression of certain genes along the pathway in the presence of elevated hepatic triglycerides. This virtual profile can serve as a biomarker of cirrhosis.

Execution of the computer model can produce various sets of outputs, and correlation analysis can be performed on the sets of outputs to generate the virtual profile of biological constituents. For example, the sets of outputs can be associated with different points in time and can represent a progression towards a particular biological state, such as, for example, the toxic state. Correlation analysis can be performed on the sets of outputs to identify a set of outputs at an earlier point in time that can serve to predict or infer the occurrence of the toxic state at a subsequent point in time. Examples of techniques for identifying biomarkers using correlation analysis are described in the co-pending and co-owned patent application to Paterson et al., entitled "Apparatus and Method for Identifying Biomarkers Using a Computer Model," U.S. application Ser. No. 10/319,779, filed Dec. 12, 2002, the disclosure of which is incorporated herein by reference in its entirety.

The experimental profile of biological constituents can be generated using values obtained from testing the therapy in the set of biological assays. In particular, the set of biological assays can be evaluated to identify biological processes that are modified by the therapy in the set of biological assays. One method of identifying the modified biological processes includes measuring levels or activities of biological constituents that are related to these modified biological processes. These levels or activities can then be used to generate the experimental profile of biological constituents.

The virtual profile of biological constituents and the experimental profile of biological constituents can be compared to determine the potential toxicity of the therapy. To facilitate comparison of the two profiles, the virtual profile and the experimental profile typically will include respective values for a common set of biological constituents. One method of comparing the two profiles includes comparing values for biological constituents associated with the two profiles. Such comparison can be done using, for example, statistical techniques. As another example, values of the two profiles can be represented graphically, and visual techniques can be used to perform the comparison. As a further example, comparison can be performed by calculating percentage differences in values of the two profiles. In some instances, a degree of correspondence of the two profiles can be determined based on comparing the two profiles, and the degree of correspondence can be used to predict the potential toxicity of the therapy. For example, if the values of the two profiles are statistically similar, then the therapy can be identified as having a high potential for inducing toxicity in the biological system. If the values of the two profiles are not statistically similar, then the therapy can be identified as having a low potential for inducing toxicity in the biological system. As discussed previously, the virtual profile of biological constituents can include a set of threshold or baseline values, and the potential toxicity of the therapy can be identified based on determining whether values of the experiment profile of biological constituents exceed or fall below the set of threshold or baseline values.

Figure 5:
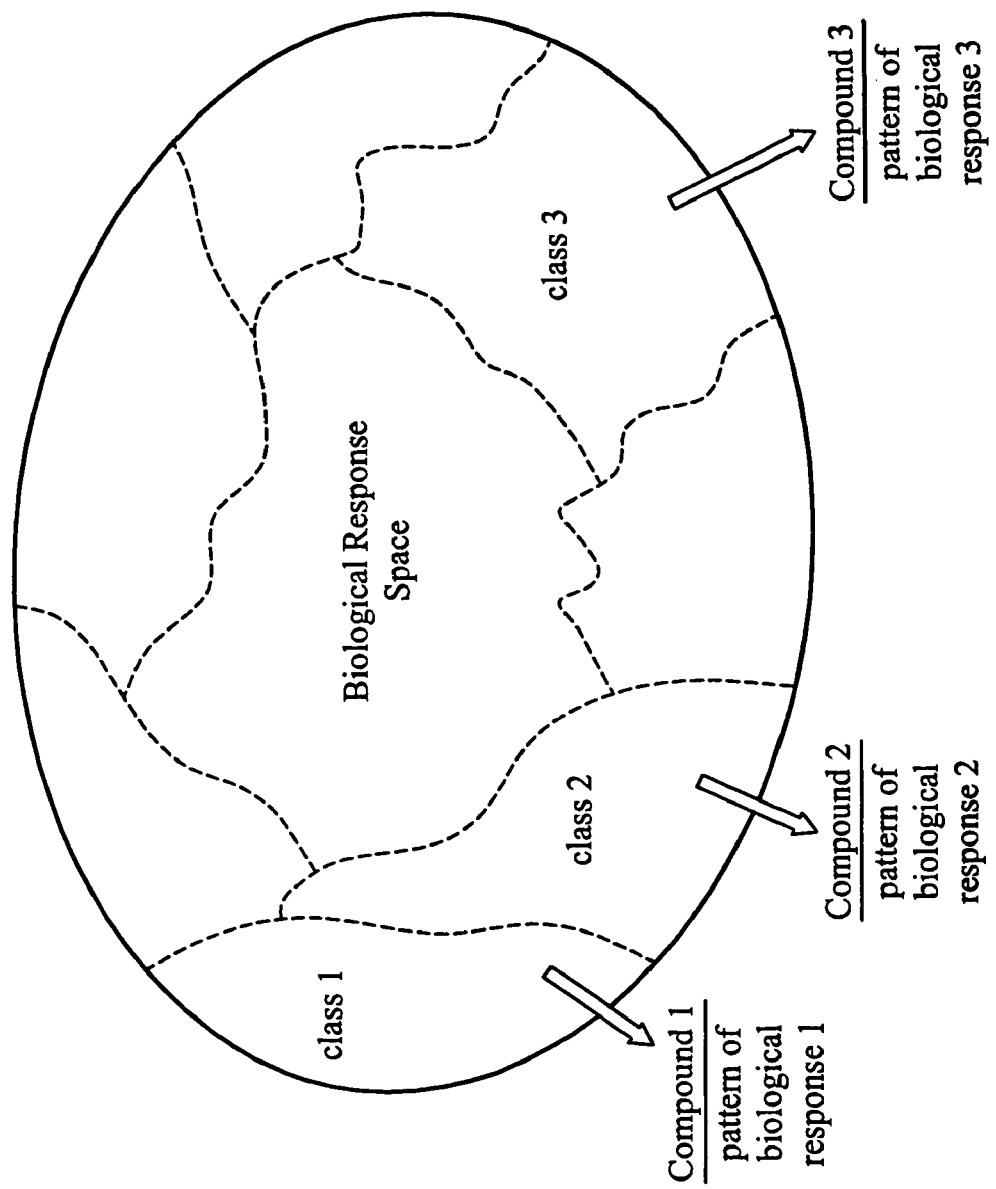
FIG. 5 shows an example of a biological response space, where various compounds are categorized based on respective patterns of biological response.

At this point, advantages associated with the methods described above can be appreciated. Advantageously, the methods can use computer models to identify a set of biological assays. The set of biological assays can be designed to adequately and accurately characterize biological response, such as, for example, biological response induced by a therapy. Results of the set of biological assays can be used to identify patterns of biological response, which patterns of biological response can then be used to categorize therapies into recognizable classes within a biological response space (e.g., classes corresponding to toxic, non-toxic, different types of toxicities, and so forth). FIG. 5 shows an example of a biological response space, where various compounds are categorized based on respective patterns of biological response. A pattern of biological response to a therapy can represent, for example, a set of biological processes modified by the therapy in a set of biological assays or an experimental profile of biological constituents. Advantageously, a therapy can be characterized based on observed biological response rather than based on biological response that is inferred from chemical characteristics.

It should be recognized that the specific methods discussed above are provided by way of example, and various other embodiments are contemplated. For example, some embodiments of the invention relate to identifying a potential toxicity of a therapy in a particular patient (e.g., a particular human patient) or a particular type of patient (e.g., a particular type of human patient). In particular, a susceptibility of a particular patient or a particular type of patient to toxicity of the therapy can be identified. Advantageously, some embodiments allow for development of biomarkers of toxicity and diagnostic biological assays to characterize and categorize patients based on their susceptibility to toxicity of a therapy.

Figure 6:
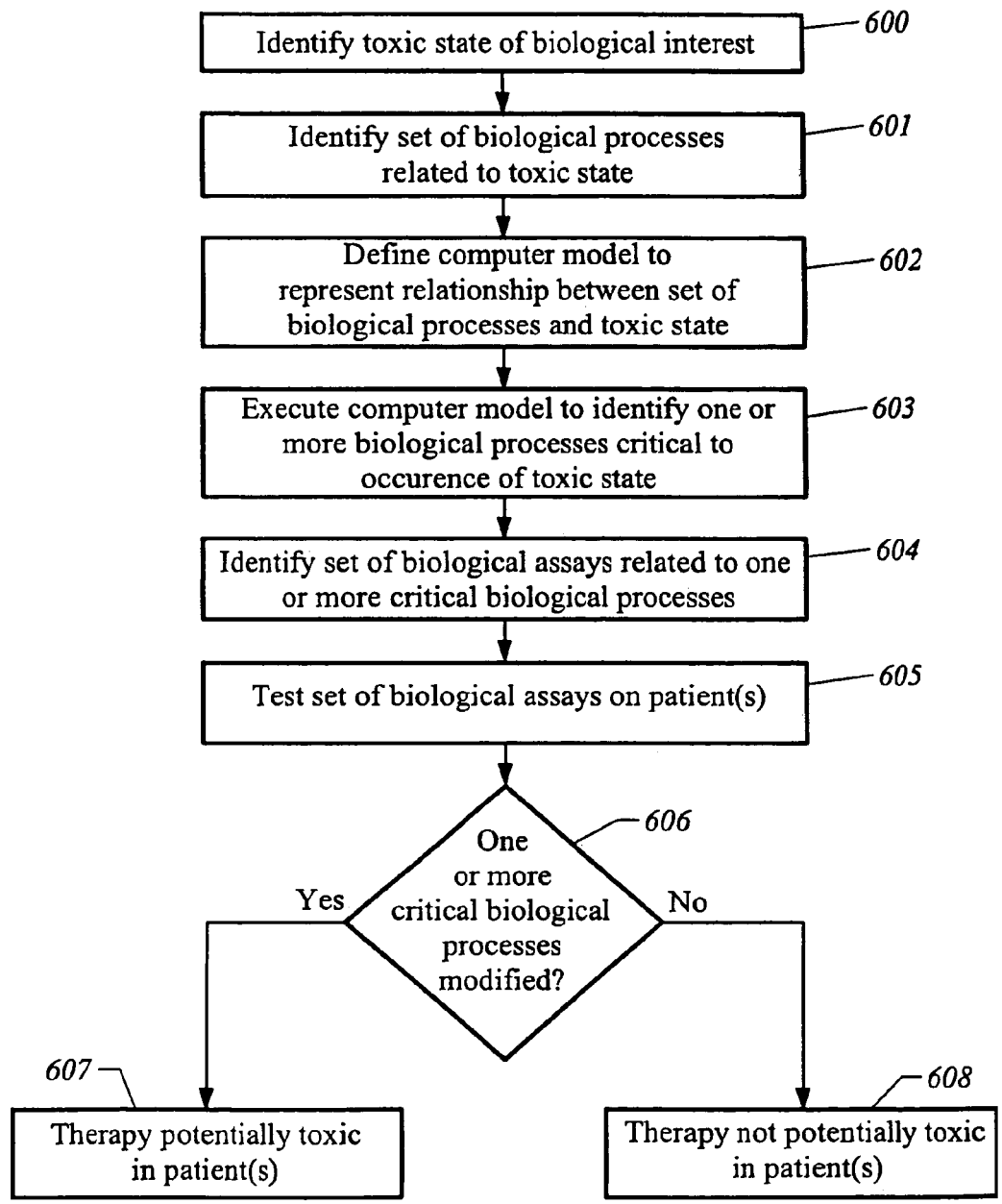
FIG. 6 shows a flow chart for identifying a potential toxicity of a therapy in a particular patient or a particular group of patients, according to an embodiment of the invention.

FIG. 6 shows a flow chart for identifying a potential toxicity of a therapy in a particular patient or a particular group of patients, according to an embodiment of the invention. At step 600, a toxic state of interest is identified. At step 601, a set of biological processes related to the toxic state is identified. At step 602, a computer model is defined to represent the set of biological processes and the interactions between the biological processes. The computer model can be defined to represent the particular patient or group of patients. In some instances, one or more configurations of the computer model can be defined to represent the particular patient or group of patients. As discussed above, a previously developed computer model can be used. At step 603, the computer model is executed to identify one or more biological processes critical to the occurrence of the toxic state. In some instances, a virtual profile of biological constituents related to the critical biological processes is generated. This virtual profile can serve as a biomarker of the toxic state. More particularly, this virtual profile can serve as a biomarker to predict or infer the occurrence of the toxic state in the particular patient or group of patients.

At step 604, a set of biological assays is identified. In some instances, the set of biological assays can serve as a diagnostic test to identify the susceptibility of the particular patient or group of patients to toxicity of the therapy. At least one biological assay from the set of biological assays is related to one or more of the biological processes identified as critical to the toxic state. In some instances, the set of biological assays can be designed based on the virtual profile of biological constituents. The set of biological assays can include, for example, measurements of in vitro physiological responses (e.g., a cell-based assay), in vivo physiological responses (e.g., an allergic scratch test), ex vivo physiological responses, genomic responses, proteomic responses, or a combination thereof. At step 605, the set of biological assays is tested on the particular patient or group of patients. The set of biological assays can be tested before or during the course of a clinical trial for the therapy. In particular, the set of biological assays can be tested prior to, subsequent to, or while applying the therapy to the particular patient or group of patients. Alternatively, or in conjunction, the set of biological assays can be tested under experimental conditions that include or simulate the presence or effects of the therapy. In some instances, an experimental profile of biological constituents can be generated from testing the set of biological assays on the particular patient or group of patients.

If one or more of the critical biological processes are modified (step 606), the therapy is identified as being potentially toxic in the particular patient or group of patients (step 607). If one or more of the critical biological processes are not modified (step 606), the therapy is identified as not being potentially toxic in the particular patient or group of patients (step 608).

Figure 7:
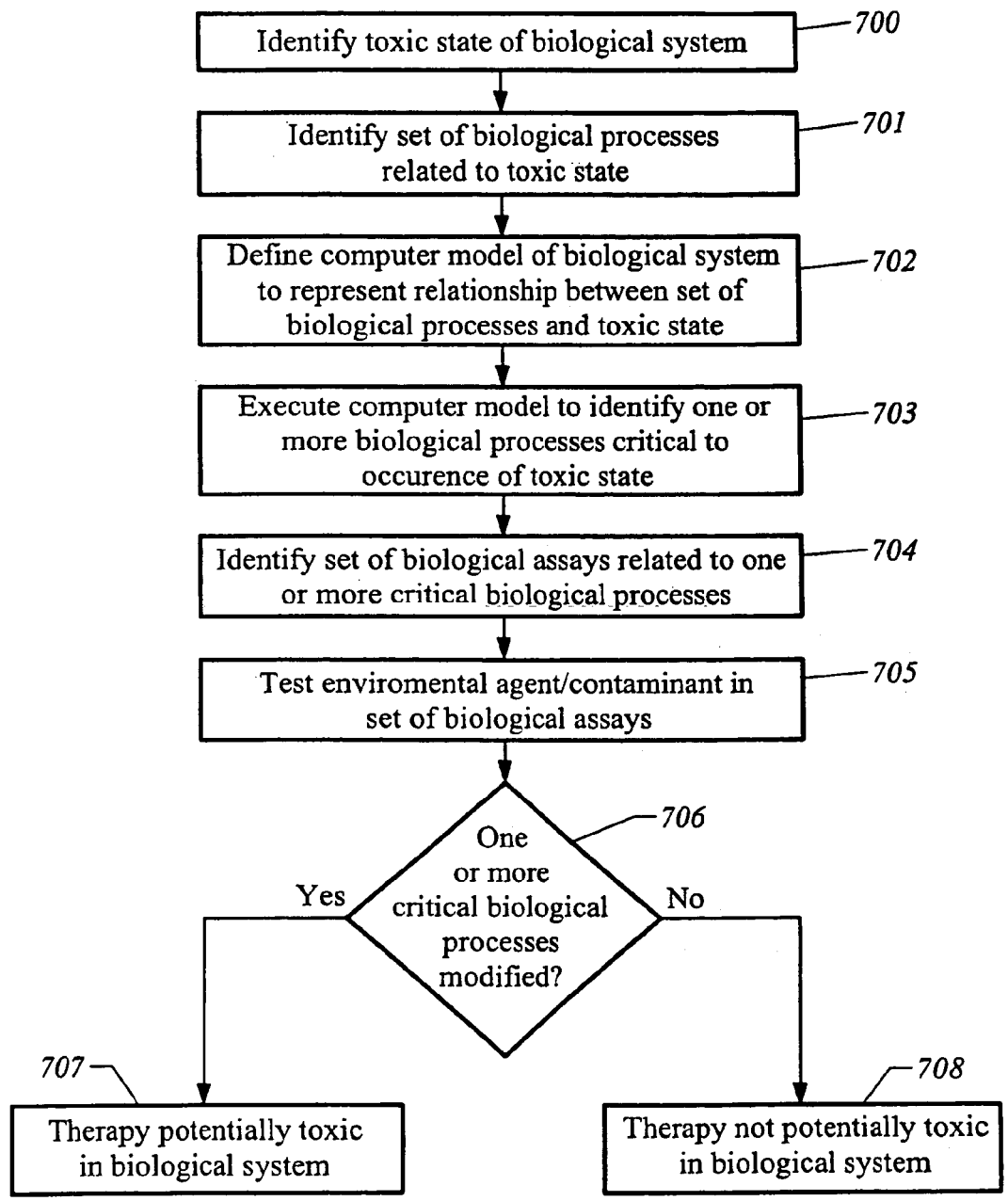
FIG. 7 shows a flow chart for identifying a potential toxicity of an environmental agent or contaminant in a biological system, according to an embodiment of the invention.

As another example, some embodiments of the invention relate to identifying a potential toxicity of a variety of other types of stimulus or perturbation that can be applied to a biological system. FIG. 7 shows a flow chart for identifying a potential toxicity of an environmental agent or contaminant in a biological system, according to an embodiment of the invention. The environmental agent or contaminant can include, for example, one or more compounds of any degree of complexity that can affect a biological state, whether by known or unknown biological mechanisms. At step 700, a toxic state of the biological system is identified. At step 701, a set of biological processes related to the toxic state is identified. At step 702, a computer model of the biological system is defined. The computer model represents the set of biological processes and the interactions between the biological processes. In some instances, a previously developed computer model of the biological system can be used. At step 703, the computer model is executed to identify one or more biological processes critical to the occurrence of the toxic state. At step 704, a set of biological assays is identified. At least one biological assay from the set of biological assays is related to one or more of the biological processes identified as critical to the toxic state. At step 705, the environmental agent or contaminant is tested in one or more of the biological assays. If one or more of the critical biological processes are modified (step 706), the environmental agent or contaminant is identified as being potentially toxic in the biological system (step 707). If one or more of the critical biological processes are not modified (step 706), the environmental agent or contaminant is identified as not being potentially toxic in the biological system (step 708).

As a further example, some embodiments of the invention relate to identifying a potential toxicity of a set of therapies in a biological system. In particular, a potential toxicity of various combinations of drugs and environmental changes can be identified. Advantageously, some embodiments allow for prediction of adverse interactions between different therapies, which adverse interactions can induce a toxic state of a biological system. In particular, some embodiments allow for prediction of adverse interactions based on execution of a computer model. As a result, adverse interactions can be predicted for various combinations of therapies without requiring each combination to be tested in a set of biological assays.

Figure 8:
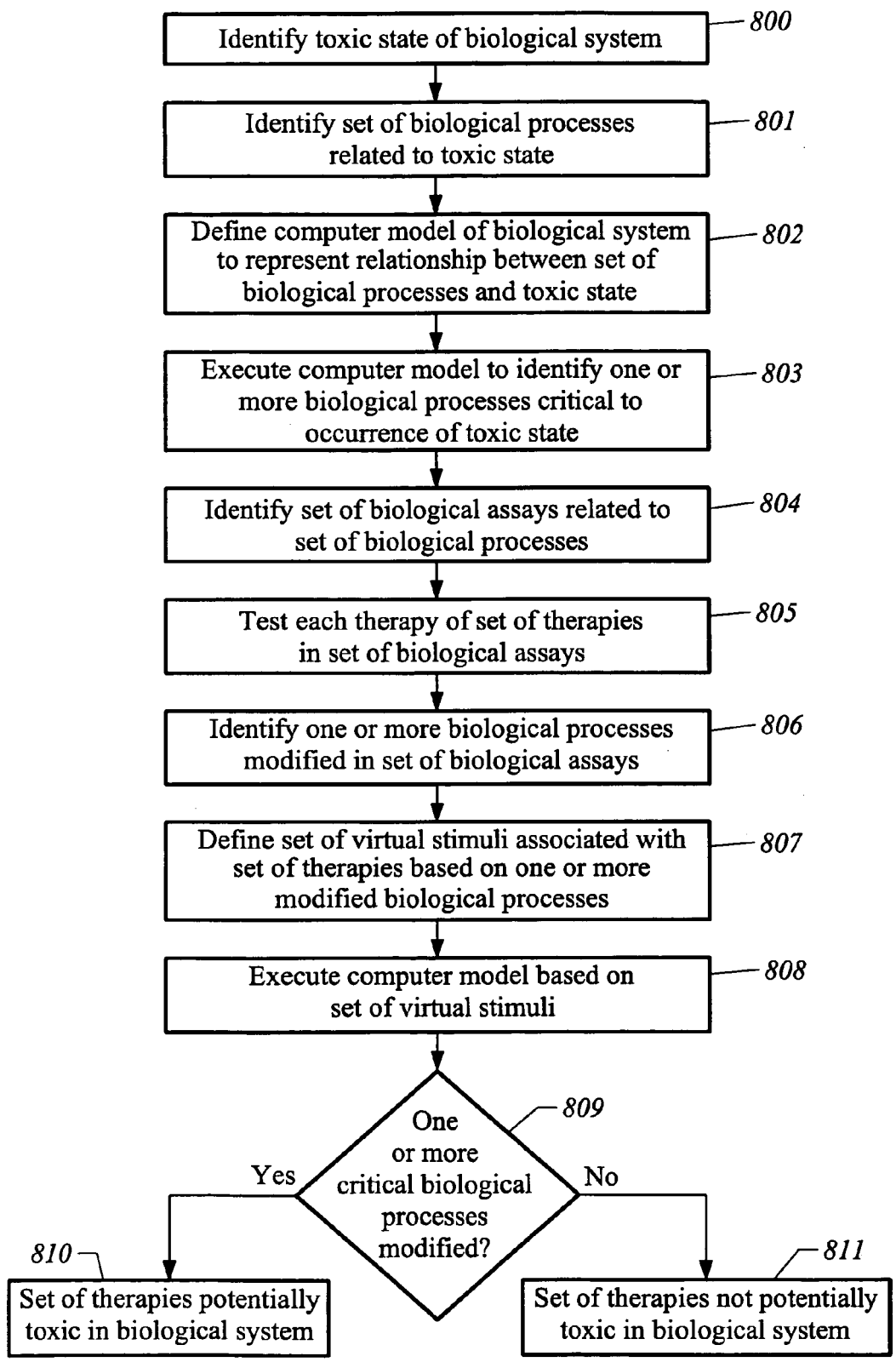
FIG. 8 shows a flow chart for identifying a potential toxicity of a set of therapies in a biological system, according to an embodiment of the invention.

FIG. 8 shows a flow chart for identifying a potential toxicity of a set of therapies in a biological system, according to an embodiment of the invention. At step 800, a toxic state of the biological system is identified. At step 801, a set of biological processes related to the toxic state is identified. At step 802, a computer model of the biological system is defined. The computer model represents the set of biological processes and the interactions between the biological processes. In some instances, a previously developed computer model of the biological system can be used. At step 803, the computer model is executed to identify one or more biological processes critical to the occurrence of the toxic state. In some instances, a virtual profile of biological constituents related to the critical biological processes is generated. This virtual profile can serve as a biomarker of the toxic state. More particularly, this virtual profile can serve as a biomarker to predict or infer the occurrence of the toxic state in the biological system.

At step 804, a set of biological assays is identified. At least one biological assay from the set of biological assays is related to one or more of the biological processes identified as being related to the toxic state. At step 805, each therapy of the set of therapies is tested in one or more of the biological assays. At step 806, the set of biological assays is evaluated to identify one or more biological processes that are modified by each therapy of the set of therapies. In some instances, an experimental profile of biological constituents can be generated for each therapy of the set of therapies. In particular, an experimental profile of biological constituents can be generated based on measuring levels or activities of biological constituents that are related to biological processes modified by a therapy.

At step 807, a set of virtual stimuli associated with the set of therapies is defined. In particular, a virtual stimulus can be defined for each therapy of the set of therapies. A virtual stimulus can be defined to represent a modification to one or more of the biological processes modified by a therapy in the set of biological assays. In some instances, a virtual stimulus can be defined for a therapy based on an experimental profile of biological constituents generated for the therapy.

At step 808, the computer model is executed based on the set of virtual stimuli. Execution of the computer model produces one or more outputs. As discussed above, outputs of the computer model typically include a set of values that represent levels or activities of biological constituents or any other behavior of the biological system. These outputs can be evaluated to predict or infer the occurrence of the toxic state. In some instances, these outputs can be compared with the virtual profile of biological constituents to produce a degree of correspondence. If one or more of the critical biological processes are modified based on execution of the computer model (step 809), the set of therapies is identified as being potentially toxic in the biological system (step 810). If one or more of the critical biological processes are not modified based on execution of the computer model (step 809), the set of therapies is identified as not being potentially toxic in the biological system (step 811). If desired, the set of therapies can be tested in one or more of the biological assays to verify the identification of the set of therapies as being potentially toxic or not potentially toxic.

It is contemplated that one or more of the steps shown in FIG. 8 can be performed for various levels or amounts of each therapy of the set of therapies to identify combinations of levels or amounts for which the set of therapies is potentially toxic. For example, one or more of the steps shown in FIG. 8 can be performed for various doses of each drug of a set of drugs to identify a combination of doses of the set of drugs for which there is a potential for toxicity. It is also contemplated that one or more of the steps shown in FIG. 8 can be performed for additional sets of therapies, including, for example, various combinations of drugs, various combinations of environmental changes, as well as various combinations of one or more drugs and one or more environmental changes. It is further contemplated that a set of experimental profiles generated for a set of therapies can be stored in a particular format, such as, for example, a database format. A set of virtual stimuli defined for the set of therapies can be similarly stored. An additional experimental profile can be generated for an additional therapy of interest, and an additional virtual stimulus can be defined based on the additional experimental profile. The computer model can be executed based on the additional virtual stimulus along with one or more previously stored virtual stimuli to identify a potential toxicity of the additional therapy in combination with one or more therapies of the set of therapies.

An embodiment of the invention relates to a computer storage product including a computer-readable medium having computer-executable code thereon for performing various computer-implemented operations. The term "computer-readable medium" is used herein to include any medium that is capable of storing or encoding a sequence of instructions or codes for performing the methods described herein. The media and code may be those specially designed and constructed for the purposes of the invention, or they may be of the kind well known and available to those having skill in the computer software arts. Examples of computer-readable media include, but are not limited to: magnetic media such as hard disks, floppy disks, and magnetic tape; optical media such as CD-ROMs and holographic devices; magneto-optical media such as floptical disks; carrier waves signals; and hardware devices that are specially configured to store and execute program code, such as application-specific integrated circuits ("ASICs"), programmable logic devices ("PLDs"), read only memories ("ROMs"), random access memories ("RAMs"), erasable programmable read only memories ("EPROMs"), and electrically erasable programmable read only memories ("EEPROMs"). Examples of computer-executable code include machine code, such as produced by a compiler, and files containing higher-level code that are executed by a computer using an interpreter. For example, an embodiment of the invention may be implemented using Java, C++, or other object-oriented programming language and development tools. Additional examples of computer-executable code include encrypted code and compressed code.

Moreover, an embodiment of the invention may be downloaded as a computer program product, where the program may be transferred from a remote computer (e.g., a server) to a requesting computer (e.g., a client) by way of data signals embodied in a carrier wave or other propagation medium via a communication link (e.g., a modem or network connection). Accordingly, as used herein, a carrier wave can be regarded as a computer-readable medium. Another embodiment of the invention may be implemented in hardwired circuitry in place of, or in combination with, machine-executable software instructions.

Example

The methods described herein can be implemented to evaluate drugs that can potentially induce cirrhosis. For example, the methods described herein can be implemented to identify effects of sulfonylurea drugs on liver metabolism. Sulfonylureas can bind to sulfonylurea receptors ("SURs") associated with ATP-sensitive potassium channels ("$K_{ATP}$ channels") in plasma membranes of liver cells. When plasma glucose level is low such as during fasting, the $K_{ATP}$ channels are open, thus keeping the liver cells hyperpolarized and limiting the entry of $Ca^{++}$ into the liver cells. When a meal is consumed, plasma glucose level rises, and glucose uptake by the liver cells causes an increased production of intracellular ATPs, which bind to the $K_{ATP}$ channels and cause the $K_{ATP}$ channels to close. When the $K_{ATP}$ channels close, the liver cells depolarize. Depolarization of the liver cells causes $Ca^{++}$ channels in the plasma membranes to open and triggers the intracellular release of $Ca^{++}$ from internal stores. The release of $Ca^{++}$ initiates migration and release of endosomal vesicles that contain insulin, and, as a result, insulin is released into circulation. This is one pathway for increasing insulin release.

An extracellular pathway for regulating the $K_{ATP}$ channels is through SURs. Binding of sulfonylureas to the SURs causes the $K_{ATP}$ channels to close, which depolarizes the liver cells, allows $Ca^{++}$ to enter the liver cells, and leads to insulin release.

Biological processes controlling dynamics and changes associated with cirrhosis are identified and are defined using a computer model of a biological system of interest. Biological constituents in the cascade of events leading to the advent of cirrhosis are also identified and are defined using the computer model.

The computer model is executed to identify one or more biological processes that are critical for cirrhosis, such as one or more biological processes shown in FIG. 3. In the case of cirrhosis, the computer model can represent a particular pathway that, under appropriate control, regulates lipid production in normal and intact hepatocytes in the liver. Execution of the computer model can show that this pathway, when over activated by the presence of an exogenous drug such as a sulfonylurea drug, results in overproduction of lipids or inhibition of lipid metabolism clearance pathway, thus leading to the symptom of "fatty liver." By evaluating outputs of the computer model, this pathway can be identified as a critical pathway that is particularly sensitive to molecular manipulation by exogenous drugs. Identifying this pathway as a critical pathway in the "cause-effect" induction of "fatty liver" serves to identify a set of biological assays that can be used to predict the occurrence of or progression towards cirrhosis in vitro.

Thus, based on outputs of the computer model, the critical pathway and biological constituents driving dynamics down the critical pathway can be identified. A virtual profile of toxicological potential can be generated by identifying signaling structures that control the dynamics of the critical pathway and physiological modifications that cells in the critical pathway undergo (e.g., changes in expression of cytokines, expression of receptors, production of lipids, and so forth). In addition, primary cell types of interest and their signaling states in the cascade of events that lead to the toxic state can be identified.

A set of whole cell biological assays can be designed by identifying the key physiological outputs of primary cell types in the critical pathway and how those cell types behave physiologically under normal homeostatic control. Given such homeostatic status quo, a set of whole cell biological assays can be designed to identify outputs when lipotoxicity takes over (e.g., overproduction of lipids and/or the inhibition of lipid metabolism) by monitoring production of free fatty acids or hepatic triglycerides. This set of biological assays can be run under particular culture conditions to simulate in vivo condition of the liver (e.g., in the presence of particular growth or control molecules). These culture conditions can be defined by control networks as represented in the computer model.

Given a family of potential biological processes active in the toxic state being studied, the set of biological assays can be designed to measure and observe modifications in one or more biological processes in vitro. The set of biological assays can include, for example, biological assays that measure cell physiology (e.g., cytokine production, receptor expression, and so forth), proteomic expression (e.g., expression and modification of cellular proteins related to the critical pathway), and genomic expression (e.g., expression of genes related to the critical pathway). For example, when designing a set of biological assays to test for effects of sulfonylurea drugs, the set of biological assays can include measurements of cellular depolarization, calcium flux, and endosomal vesicle release. If it is determined that genomic changes are also associated with the effects of sulfonylurea drugs, gene expression techniques can also be employed.

Once the set of biological assays is identified, the sulfonylurea drugs can be tested in the set of biological assays. Biological assays can be run on the sulfonylurea drugs in a dose-dependent manner to establish toxic dose levels for eventual calculation of a therapeutic index. Based on the pattern of biological responses observed in the set of biological assays, drugs that are potentially toxic and the doses at which toxicities become incident can be identified. As used herein, the term "therapeutic index" refers to a measure of safety of a therapy. In some instances, a therapeutic index represents a relationship between an efficacious dose and a toxic dose of a therapy. In particular, a therapeutic index can be provided as a ratio of an efficacious dose and a toxic dose of a therapy. A ratio of an efficacious dose and a toxic dose is sometimes expressed as a "fold difference." For example, to meet regulatory standards, an efficacious dose is desirably 10-fold lower or at least 100-fold lower than a toxic dose. A ratio of an efficacious dose and a toxic dose can also be expressed as a difference in a logarithmic scale. For example, a "3 log separation" can characterize a therapy having an efficacious dose that is 1000 times lower than a toxic dose of the therapy. Typically, an efficacious dose of a therapy is derived from a dose response curve and is expressed in terms of a quantity labeled as ED50. ED50 can correspond to a dose at which 50 percent of a therapeutic effect is observed (e.g., a mean arterial blood pressure decrease of 10% relative to 20% decrease for a full therapeutic effect) or at which 50 percent of patients respond to a therapy. Typically, a toxic dose of a therapy is derived based on a particular toxic state and a particular therapeutic endpoint involved and is expressed in terms of a quantity labeled as TD50. TD50 can correspond to a dose at which 50 percent of patients exhibit a toxic state (e.g., 50 percent of patients having a white blood cell count depleted below a particular threshold value). When a toxic state is associated with death, a toxic dose can be expressed in terms of a quantity labeled as LD. An example of LD is LD10, which corresponds to a dose at which 10 percent of patients die.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the invention has been described with reference to the specific embodiments thereof, it should be understood by those skilled in the art that various changes may be made and equivalents may be substituted without departing from the true spirit and scope of the invention as defined by the claims. In addition, many modifications may be made to adapt a particular situation, material, composition of matter, method, process operation or operations, to the spirit and scope of the invention. All such modifications are intended to be within the scope of the claims. In particular, while the methods disclosed herein have been described with reference to particular operations performed in a particular order, it will be understood that these operations may be combined, sub-divided, or re-ordered to form an equivalent method without departing from the teachings of the invention. Accordingly, unless specifically indicated herein, the order and grouping of the operations is not a limitation of the invention.

What is claimed is:

1. A method to identify a potential toxicity of a therapy in a biological system, the method using a computer model that represents a plurality of biological processes of the biological system, wherein each biological process interacts according to a biological mechanism with one or more additional biological processes of the biological system, the method comprising:
   executing the computer model to identify a first set of biological processes contributing to occurrence of a toxic state of the biological system;
   identifying a set of biological assays based on the first set of biological processes;
   testing the therapy in the set of biological assays to identify a second set of biological processes modified by the therapy; and
   identifying the potential toxicity of the therapy based on the second set of biological processes.

2. The method of claim 1, wherein identifying the potential toxicity of the therapy includes comparing the first set of biological processes and the second set of biological processes.

3. The method of claim 1, wherein the biological system includes an organ.

4. The method of claim 3, wherein the organ is a mammalian liver.

5. A method to identify a potential toxicity of a therapy in a biological system, the method using a computer model that represents a plurality of biological processes related to a toxic state of the biological system, wherein each biological process interacts according to a biological mechanism with one or more additional biological processes of the biological system, the computer model being configured to evaluate an effect of each biological process of the plurality of biological processes on the toxic state, the method comprising:
   executing the computer model to identify a first set of biological processes, each biological process of the first set of biological processes being modified during occurrence of the toxic state;
   identifying a set of biological assays, at least one biological assay of the set of biological assays being related to at least one biological process of the first set of biological processes;
   testing the therapy in at least one biological assay from the set of biological assays to identify a second set of biological processes, each biological process of the second set of biological processes being modified in the set of biological assays;
   comparing the first set of biological processes and the second set of biological processes to produce a degree of correspondence; and
   predicting the potential toxicity of the therapy based on the degree of correspondence.

6. The method of claim 5, wherein the set of biological assays includes a cell-based assay.

7. A method to identify a potential toxicity of a therapy in a biological system, the method comprising:
   executing a computer model that represents a plurality of biological processes of the biological system, wherein each biological process interacts according to a biological mechanism with one or more additional biological processes of the biological system, to identify a first set of biological processes related to a toxic state of the biological system;
   identifying a set of biological assays based on the first set of biological processes;
   testing the therapy in the set of biological assays to identify a second set of biological processes modified in the set of biological assays; and comparing the first set of biological processes and the second set of biological processes to identify the potential toxicity of the therapy.

8. The method of claim 7, wherein the computer model represents the first set of biological processes using at least one mathematical relation.

9. The method of claim 7, wherein comparing the first set of biological processes and the second set of biological processes includes producing a degree of correspondence of the first set of biological processes and the second set of biological processes.

10. A method to identify a potential toxicity of a therapy in a biological system, the method using a computer model that represents a plurality of biological processes of the biological system, wherein each biological process interacts according to a biological mechanism with one or more additional biological processes of the biological system, the method comprising:
   identifying a set of biological processes related to a toxic state of the biological system, the set of biological processes being identified by executing the computer model;
   generating a virtual profile of a set of biological constituents, the set of biological constituents being associated with the set of biological processes;
   identifying a set of biological assays based on the set of biological constituents;
   testing the therapy in the set of biological assays to generate an experimental profile of the set of biological constituents;
   comparing the virtual profile of the set of biological constituents and the experimental profile of the set of biological constituents to produce a degree of correspondence; and
   predicting the toxicity of the therapy based on the degree of correspondence.

11. The method of claim 10, wherein the therapy includes at least one drug.

12. A method to identify a potential toxicity of a drug in a biological system, the method comprising:
   receiving a computer model-based identification of at least one critical biological process, the at least one critical biological process contributing to occurrence of a toxic state of the biological system;
   identifying a set of biological assays associated with the at least one critical biological process, wherein each biological process interacts according to a biological mechanism with one or more additional biological processes of the biological system;
   testing the drug in the set of biological assays to identify at least one biological process modified in the set of biological assays; and
   identifying the potential toxicity of the drug based on the at least one biological process modified in the set of biological assays.

* * * * *